United States Patent
Yoo et al.

(10) Patent No.: US 7,615,145 B2
(45) Date of Patent: Nov. 10, 2009

(54) ONE-POT PROCESS FOR THE REDUCTION OF SULFUR, NITROGEN AND THE PRODUCTION OF USEFUL OXYGENATES FROM HYDROCARBON MATERIALS VIA ONE-POT SELECTIVE OXIDATION

(75) Inventors: Jin S. Yoo, Flossmoor, IL (US); Sang-Chul Lee, Asan-si (KR); Ho Dong Kim, Gangneung-si (KR)

(73) Assignee: Kocat Inc., Seoul (KR)

( * ) Notice: Subject to any disclaimer, the term of this patent is extended or adjusted under 35 U.S.C. 154(b) by 200 days.

(21) Appl. No.: 11/870,820

(22) Filed: Oct. 11, 2007

(65) Prior Publication Data

US 2008/0149533 A1  Jun. 26, 2008

Related U.S. Application Data

(60) Provisional application No. 60/851,052, filed on Oct. 12, 2006.

(30) Foreign Application Priority Data

Jun. 11, 2007   (KR) .................. 10-2007-0056781
Jun. 25, 2007   (KR) .................. 10-2007-0062496
Aug. 6, 2007    (KR) .................. 10-2007-0078542

(51) Int. Cl.
*C10G 17/00*   (2006.01)
*C10G 45/04*   (2006.01)

(52) U.S. Cl. .................. 208/208 R; 208/243; 208/244; 208/245; 208/295; 562/412; 562/413

(58) Field of Classification Search ......... 562/412–413; 208/208 R, 243–244, 295
See application file for complete search history.

(56) References Cited

U.S. PATENT DOCUMENTS

2002/0193631 A1* 12/2002 Park et al. .................. 562/416

OTHER PUBLICATIONS

Haas, G.R. et al (1998). Organometallics, 17, 20, pp. 4454-4460.*

* cited by examiner

*Primary Examiner*—Robert J Hill, Jr.
*Assistant Examiner*—Brian McCaig
(74) *Attorney, Agent, or Firm*—Rothwell, Figg, Ernst & Manbeck, P.C.

(57) ABSTRACT

The present invention relates to a process of reducing sulfur- or nitrogen-containing compounds and producing oxygenates, and in particular to a one-pot process of reducing sulfur- or nitrogen-containing compounds and also producing oxygenates in the presence of a homogeneous catalyst such as $M^{n+}$/a first solvent or $M_1^{n+}$/a second solvent/$M_2^{m+}$/a third solvent or a mixture thereof, the process herein being useful as an excellent octane booster in the reformulated gasoline and as a cetane booster for the future oxygenated diesel in a one-pot reaction.

16 Claims, 1 Drawing Sheet

ONE-POT PROCESS FOR THE REDUCTION OF SULFUR, NITROGEN AND THE PRODUCTION OF USEFUL OXYGENATES FROM HYDROCARBON MATERIALS VIA ONE-POT SELECTIVE OXIDATION

CROSS REFERENCE TO RELATED APPLICATIONS

This application claims priority from Korean patent application No. 10-2007-56781 filed on Jun. 11, 2007, Korean patent application No. 10-2007-0062496 filed on Jun. 25, 2007 and Korean patent application No. 10-2007-78542 filed on Aug. 6, 2007, and claims benefit of U.S. provisional application No. 60/851,052 filed on Oct. 12, 2006, all of which are incorporated herein in its entirety.

TECHNICAL FIELD

The present invention relates to a process of reducing sulfur- or nitrogen-containing compounds and producing oxygenates, and in particular to a one-pot process of reducing sulfur- or nitrogen-containing compounds and also producing oxygenates in the presence of a homogeneous catalyst such as $M^{n+}/a$ first solvent or $M_1^{n+}/a$ second solvent/$M_2^{m+}/a$ third solvent or a mixture thereof, the process herein being useful as an excellent octane booster in the reformulated gasoline and as a cetane booster for the future oxygenated diesel in a one-pot reaction.

RELATED PRIOR ART

Hydrocarbon substrate (e.g., petroleum) contains elemental sulfur and organic aliphatic sulfur compounds such as thiols, sulfides and disulfides, which are generally labile and easily removed by a thermal treatment and other conventional hydrotreating processes.

The conventional hydrodesulfurization (referred to as 'HDS' hereinafter) process technology has been remarkably advanced through the fierce worldwide competition among petroleum refiners as well as academic endeavors, and became a key pivotal process for the petroleum refineries for removing sulfur to meet the stringent air pollution control regulation enacted by European countries, the United States and Japan.

Especially, spearheaded by EU countries, the near zero sulfur level (10 ppm S) in the transportation fuels, in particular gasoline, has already been targeted in some European countries. In order to meet the above objective, it is required to develop a deep and/or ultra-deep desulfurization technology. As shown below, a dramatic shift to super clean fuel also occurred in the sulfur regulation for the transportation fuel in South Korea as well.

TABLE 1

| Year | 2006 | 2008 | 2010 |
|---|---|---|---|
| Gasoline, ppm S | 130 | 50 | 10 |
| Diesel oil, ppm S | 430 | 30 | 10 |

However, there are also other forms of organic sulfur like a series of thiophenes and their condensed derivatives, which become increasingly difficult to remove from the hydrocarbon fraction in petroleum.

Among the condensed thiophene derivatives, generally benzothiophenes present in gasoline and the more condensed sulfur compounds, e.g., dibenzothiophene, 4-methyldibenzothiophene, in particular 4,6-dimethyldibenzothiophene, are found in diesel fuel, the HDS middle distillates, heavier fractions, and residual bottoms of petroleum crudes. Dibenzothiophene and its alkyl derivatives are called as a 'refractory' sulfur compound simply because they are thermally stable at the elevated temperature (650° C.), and are also very difficult to remove by the conventional refinery processes such as the HDS process.

For this reason, it is extremely difficult to meet the near zero sulfur target even with the most advanced HDS catalyst technology, due to the difficult barrier inherent to the fundamental chemistry involved in the current HDS process.

There have been many reports on experimental HDS catalysts that can meet the above objective. However, the HDS process conditions required for these processes are so severe that the essential hydrocarbon components such as olefins, paraffin and aromatics including multi-ring compounds are excessively hydrogenated by consuming an enormous amount of expensive hydrogen. Besides, the resulting HDS product loses a substantial volume by forming the gas products and excessively hydrogenated products. They become no longer a viable transportation fuel due to the significant loss of octane number (for gasoline) or cetane number (for diesel). Consequently, an additional processes, e.g., cracking reaction and blending procedure with special oxygenates should be performed to restore the desired physical and chemical properties such as octane number in the case of gasoline and to meet the oxygen content required by the reformulated gasoline and the future oxygenated diesel, respectively.

DETAILED DESCRIPTION

To overcome the aforementioned problems of the conventional HDS technology, the present invention aims to provide a process for removing the refractory sulfur compounds or at least selectively oxidizing the sulfur compounds, in particular refractory sulfur compounds such as dibenzothiophene and 4,6-dimethyldibenzothiophene, into sulfoxide and sulfone, and the N-moieties into N-oxide and oxime, etc., which are relatively easier to remove.

The process herein also allows to a further oxidation of benzylic and/or allylic compounds contained in the hydrocarbon substrates to form alcohols, ketones, which can be used as an excellent octane booster in the reformulated gasoline and as a cetane booster for the future oxygenated diesel in a controlled oxidation reaction.

According to an aspect of the present invention, there is provided a one-pot process for reducing a sulfur- or nitrogen-containing compound and producing an oxygenate in a hydrocarbon substrate, which comprises the steps of (a) placing a non-MC-type homogeneous catalyst in a reactor; (b) adding the hydrocarbon substrate in the reactor; and (c) introducing an oxidant into the reactor.

According to another aspect of the present invention, there is provided a one-pot process for reducing a sulfur- or a nitrogen-containing compound and producing an oxygenate in a hydrocarbon substrate, which comprises (a) converting the sulfur- or the nitrogen-containing compound in the hydrocarbon substrate into a sulfur- or nitrogen-containing precursor, respectively, and also converting a benzylic or an allylic compound in the hydrocarbon substrate into the oxygenate at the same time via a selective oxidation of the hydrocarbon substrate in the presence of a non-MC-type homogeneous catalyst and an oxidant; and (b) conducting a post-treatment selected from the group consisting of filtration, fractionation, selective adsorption, solvent extraction, catalytic destruction, selective oxidation, pyrolysis and a combination thereof.

Four functions, i.e., desulfurization, denitrogenation, demetallation and production of oxygenates, may be attained according to various embodiments of the present invention. It is noteworthy that the level of the four functions may be controlled by varying the oxidant/S ratio. This is important in that it is required to modify the oxidation conditions to meet the environmental requirements of near zero content of sulfur and nitrogen and 0.5-5% oxygen in the reformulated gasoline as well as oxygenated diesel of next-generation.

According to an embodiment of the present invention, there is provided a one-pot process for reducing a sulfur- or nitrogen-containing compound and producing an oxygenate in a hydrocarbon substrate, which comprises (a) placing a non-MC-type homogeneous catalyst in a biphasic system; (b) adding the hydrocarbon substrate in the biphasic system; and (c) introducing an oxidant into the biphasic system.

According to another embodiment of the present invention, there is provided a one-pot process for reducing a sulfur- or nitrogen-containing compound and producing an oxygenate in a hydrocarbon substrate, which comprises (a) converting the sulfur- or the nitrogen-containing compound in the hydrocarbon substrate into a sulfur- or a nitrogen-containing precursor and also converting a benzylic or an allylic compound in the hydrocarbon substrate into the oxygenate at the same time via selective oxidation of the hydrocarbon substrate in a biphasic system comprising a non-MC-type homogeneous catalyst and an oxidant; and (b) removing a layer that comprises a sulfur- or nitrogen-containing precursor.

Through the selective oxidation, oxygenates that increase an octane number (gasoline) and a cetane number (diesel oil) may be produced, and a nitrogen- or sulfur-containing compound may also be converted into a nitrogen- or sulfur-containing precursor that may be separated or removed relatively easily, thus enabling to accomplish the deep and/or ultra-deep desulfurization and denitrogenation.

To effectively remove such sulfur-containing compounds, dealkylation and/or isomerization reactions, i.e., shifting two methyl groups from 4- and 6-positions to other positions, should precede to circumvent the steric effect for the effective sulfur removal reaction to occur. However, the fundamental problem with the conventional HDS technology lies in the fact that 4,6-dimethyldibenzothiophene is the most difficult compound for desulfurization due to the steric hindrance effect posed by two methyl groups in 4- and 6-positions surrounding the sulfur atom in the structure of the substrate. In short, the conventional HDS technology has a critical limitation even with the most advanced version of the HDS catalyst to attain an economically and technically viable process for deep or ultra-deep desulfurization to meet the near zero sulfur target.

Contrary to the steric hindrance effect posed by the structure of 4,6-dimethyldibenzothiophene in the HDS process, the electron releasing function of two methyl groups in 4- and 6-positions in the substrate molecule enhances the electron density on the sulfur atom as shown in Table 2 below, and thus it becomes more vulnerable to the electrophilic attack such as oxidation reaction.

TABLE 2

(Energy & Fuels 2000, 14, 1232-1239)

| Sulfur compound | Formulas | Electron density | K(L/mol × minute) |
|---|---|---|---|
| Methylphenyl sulfide | | 5.915 | 0.295 |
| Thiophenol | | 5.902 | 0.270 |
| Diphenyl sulfide | | 5.860 | 0.156 |
| 4,6-DMDBT | | 5.760 | 0.0767 |
| 4-MDBT | | 5.759 | 0.0627 |
| Dibenzothiophene | | 5.758 | 0.0460 |

TABLE 2-continued (Energy & Fuels 2000, 14, 1232-1239)

| Sulfur compound | Formulas | Electron density | K(L/mol × minute) |
| --- | --- | --- | --- |
| 1-Benzothiophene | 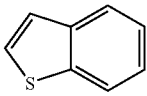 | 5.739 | 0.00574 |
| 2,5-Dimethylthiophene | 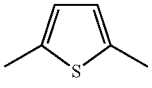 | 5.716 | — |
| 2-Methylthiophene | 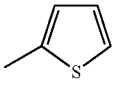 | 5.706 | — |
| Thiophene |  | 5.696 | — |

Thus, the reactivity tread of the refractory sulfur compounds, DBT and its alkyl derivatives, toward the selective sulfoxidation process becomes exactly opposite to that observed in the conventional HDS reaction. The most refractory sulfur compound, 4,6-dimethyldibenzothiophene, which is stable at an elevated temperature (650° C.) and resistant to desulfurization even under the extreme conditions of the HDS process, becomes the easiest substrates for the oxidative desulfurization (referred to as 'ODS' herein after) process as shown below.

ldibenzothiophene (4,6-DMDBT) in a similar homogeneous catalyst system containing a transition metal ion (see scheme 1 below).

Further, contrary to the oxygen atom, the sulfur atom can form various compounds by expanding its oxidation state. For example, dibenzothiophene is oxidized to sulfoxide and then to sulfone consecutively in the selective oxidation systems, as illustrated below. In this oxidation process, the physical properties such as a boiling point, a molecular polarity and chemi-

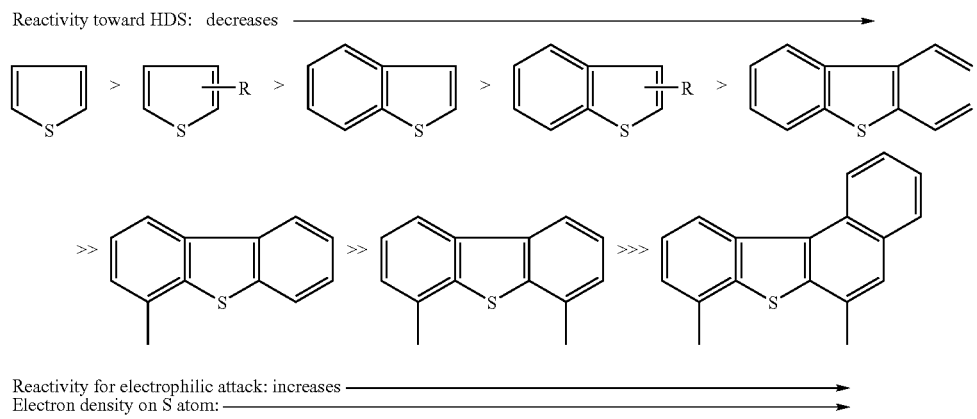

Reactivity toward HDS: decreases →
Reactivity for electrophilic attack: increases →
Electron density on S atom: →

For non-thiophenic sulfur compounds, the electron density on the sulfur atom increases in a direction of diphenyl sulfide<thiophenol<methyl phenyl sulfide, as shown in above. Consequently, the elelctrophilic attack such as the selective oxidation reaction proceeds in the same trend as that observed in the electron density on the sulfur atom in the oxirane soluble Mo-catalyst. The same chemical principle can also be applied to the selective oxidation of a series of thiophenic derivatives, in particular, refractory dibenzothionphene (DBT), 4-alkylbenzene (4-MDBT) and 4,6-dialkycal properties of the oxidized products (i.e., dibenzothiophene sulfoxide and sulfone) are greatly altered.

Utilizing these changes in the physical properties induced by the selective oxidation reaction, the removal of the sulfur impurities could readily be achieved by means of the physical separation techniques such as a fractionation, a solvent extraction and a selective adsorption. Also, the sulfoxide and sulfone products become much more polar and labile, and at the same time, they are also quite labile in extruding SO- and $SO_2$-moieties from the oxidized sulfoxide and sulfones respectively over a variety of catalysts including the chemical destruction catalyst such as base materials.

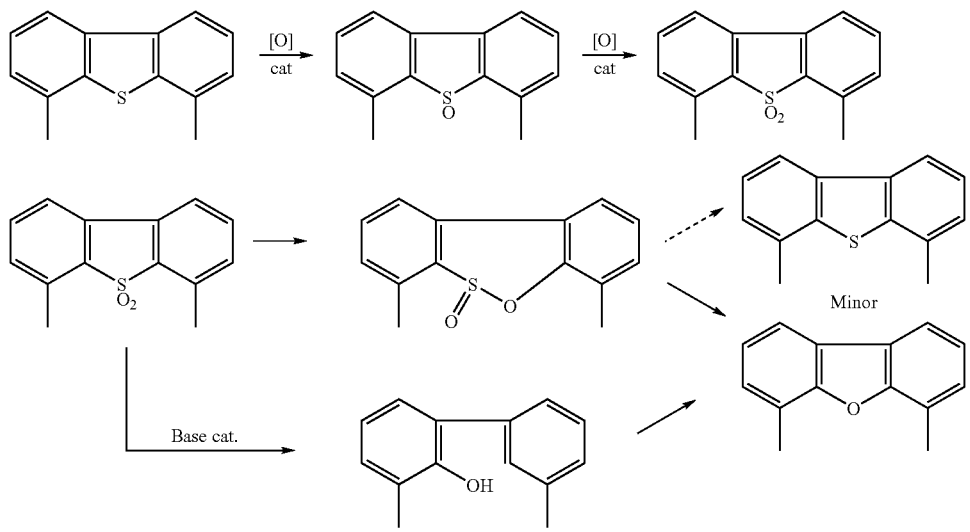

Scheme 1: Desulfurization of 4,6-DMDBT sulfone by means of a base catalyst

The present invention provides a process for oxidizing the sulfur compounds selectively, in particular refractory sulfur compounds such as dibenzothiophene and 4,6-dimethyldibenzothiophene, to sulfur-containing precursors such as sulfoxide and sulfone, and also oxidizing the N-moieties to nitrogen-containing precursors such as N-oxide and oxime etc. Thus oxidized sulfur- or nitrogen-containing precursors may be easily removed by consecutively conducting various procedures described herein or by conducting selective oxidation in a biphasic system.

The process herein also allows a further oxidation of the hydrocarbon substrates containing the benzylic and/or allylic carbon to form alcohols, aldehydes and ketones, which can be used as an excellent octane booster in the reformulated gasoline and as a cetane booster for the future oxygenated diesel in a controlled oxidation reaction.

As described above, the removal or separation of sulfur- or nitrogen-containing compounds may be conducted as a separate step or at the same time with the selective oxidation. Therefore, according to another aspect of the present invention, there is provided a process for selectively oxidizing a hydrocarbon substrate, which comprises the oxidation of the hydrocarbon substrate in a biphasic system containing a non-MC-type homogeneous catalyst and an oxidant, thereby converting a sulfur- or nitrogen-containing compound in the hydrocarbon substrate into a sulfur- or nitrogen-containing precursor, respectively, and also converting a benzylic or an allylic compounds into oxygenates at the same time.

According to still another aspect of the present invention, there is provided a process for selectively oxidizing a hydrocarbon substrate, which comprises: (a) converting a sulfur- or nitrogen-containing compound in the hydrocarbon substrate into a sulfur- or a nitrogen-containing precursor, respectively; and (b) converting a benzylic or allylic compound into oxygenates at the same time; where the steps (a) and (b) are conducted through a selective oxidation of the hydrocarbon substrate in a biphasic system containing a non-MC-type homogeneous catalyst and an oxidant.

The sulfur- or nitrogen-containing hydrocarbons and allylic or benzylic hydrocarbons moves into a polar solvent layer such as an aqueous solution or an acetic acid-water layer, and may be removed relatively easily as illustrated below. (i) DBT (or 4,6-DMDBT), (ii) indole and (iii) tetralin are model compounds of (i) a sulfur-containing compound, (ii) a nitrogen-containing compound and (iii) an allylic or benzylic compound, respectively.

Scheme 2
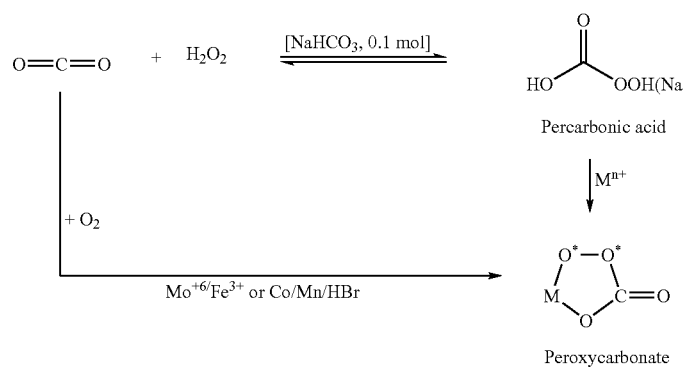
Scheme 3: Selective extraction in a biphasic system
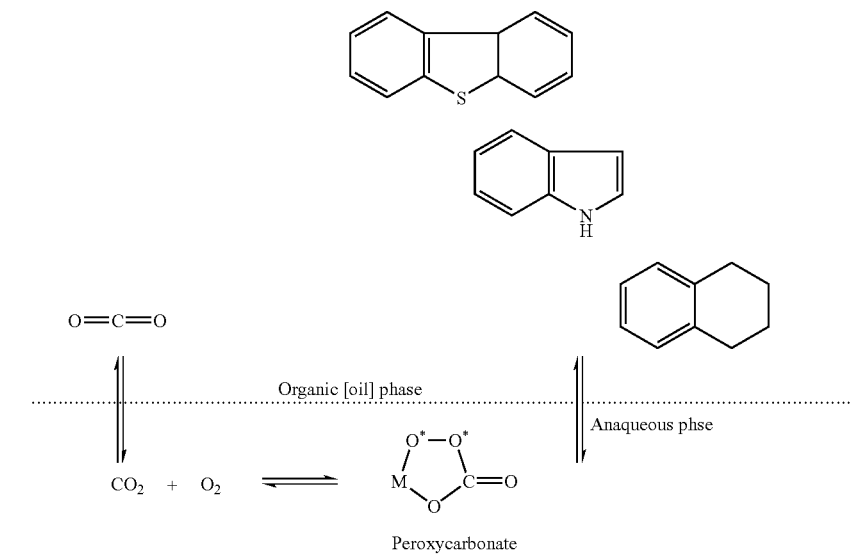
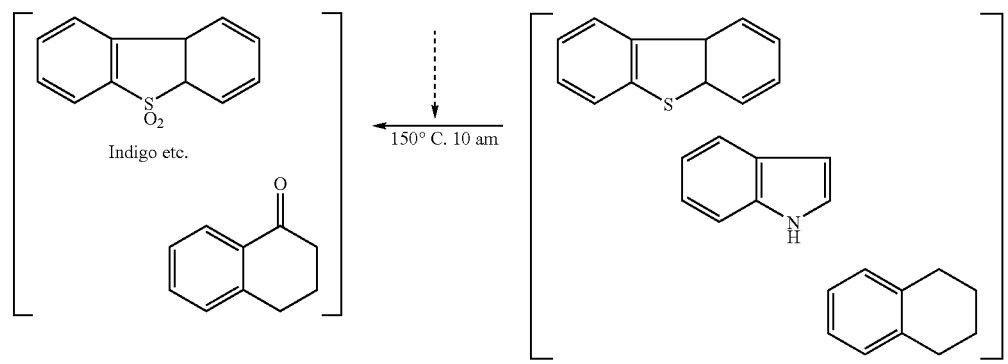

If the nitrogen-containing compound in hydrocarbon substrate exceeds a certain amount, it may hamper the selective oxidation. Thus, a process herein may further comprise the pretreatment step of partially removing a nitrogen-containing compound in the hydrocarbon substrate prior to the selective oxidation. The pretreatment may be conducted by using an absorbent or an excess of a non-MC-type homogeneous catalyst as because a non-MC-type homogeneous catalyst may also serve as the absorbent.

As used herein, the term "one-pot process" refers to a process comprising simultaneously or successively adding all reactants into a reactor to have them react together, in which no separation and/or purification of the intermediate state is required before the final product is produced. Sulfur- or nitrogen-containing precursors as defined herein may also be considered as such product as they do not need to be separated and/or removed during the reaction or the process; they are easily separated and/or removed after the reaction is completed.

As used herein, the term "non-MC-type homogeneous catalyst" or "homogeneous catalyst" refers to a $M^{n+}$/a first solvent or a $M_1^{n+}$/a second solvent/$M_2^{m+}$/a third solvent;

In the present invention, $M^{n+}$ is selected among $Co^{3+}$, $Mo^{6+}$, $MoO_2^{2+}$, $MoO^{4+}$, $MoO_4^{2-}$, $V^{5+}$, $VO^{3+}$, $VO_2^{3+}$, $W^{6+}$, $WO_4^{2-}$, $Cr^{3+}$, $Ti^{4+}$, $Fe^{3+}$, $Ni^{2+}$, $Zr^{4+}$, $ZrO^{2+}$, $Hf^{4+}$, $Ta^{6+}$, $Nb^{5+}$, $Ce^{4+}$ and $Ce^{3+}$;

$M_1^{n+}$ is selected among $Co^{3+}$, $Mo^{6+}$, $MoO_2^{2+}$, $MoO^{4+}$ and $MoO_4^{2-}$; and $M_2^{m+}$ is selected among $Co^{3+}$, $Fe^{3+}$, $Ni^{2+}$, $Cu^{2+}$, $V^{5+}$, $VO^{3+}$, $VO_2^{3+}$, $Cr^{3+}$, $Ti^{4+}$, $Zr^{4+}$, $ZrO^{2+}$, $Hf^{4+}$, $Ta^{6+}$, $Nb^{5+}$, $Re^{4+}$, $Ru^{4+}$, $Sm^{4+}$, $Pr^{3+}$ and $Ce^{3+}$.

Considering the activity of a catalyst, conversion, yield and selectivity, each of the $M^{n+}$ and the $M_1^{n+}$ is preferred to be a Mo-based metal ion such as $Mo^{6+}$, $MoO_2^{2+}$, $MoO^{4+}$ and $MoO_4^{2-}$ or a V-based metal ion such as $V^{5+}$, $VO^{3+}$ and $VO_2^{3+}$. The Mo-based metal ion is most preferred.

In the present invention, a first solvent, a second solvent and a third solvent are the same or different and each is independently selected among water, alcohols, $CH_3CN$, DMF, N-pyrrolodone, formic acid, acetic acid, octanoic acid, trifluoroacetic acid, acetic acid-water mixture, aliphatic or aromatic $C_6$-$C_{16}$ hydrocarbon, H-donor solvent, diesel oil, gasoline, LCO and a mixture thereof. Considering the activity of a catalyst, conversion, yield and selectivity, each of the second solvent and the third solvent is preferred to be alcohols such as TBA.

In the present invention, a second solvent/a third solvent is preferred to be a miscible or compatible solvent pair such as a polar/polar and a nonpolar/nonpolar solvent pair. A solvent pair with poor compatibility such as TBA/benzene is not preferred. It is obvious that one skilled in the art may easily select the solvent pair of a second solvent/a third solvent and apply it to the present invention on the basis of the disclosure of the present invention along with the experimental results herein.

As used herein, an "oxidant" or a selective oxidation system of "homogeneous catalyst-oxidant" controls the degree of selective oxidation of hydrocarbon substrate in the present invention. Examples of the oxidant herein include but are not limited to an $O_2/CO_2$ mixture, $H_2O_2$, t-butylhydroperoxide (TBHP), $H_2O_2/HCOOH$, $H_2O_2/CF_3COOH$, ethylbenzene hydroperoxide, cumyl hydroperoxide, cyclohexylperoxodicarbonate $(C_6H_{11})_2C_2O_6$, $H_2O_2$/heteropolyacid ($H_3PMo_{12}O_{40}$, $H_3PW_{12}O_{40}$, $H_{0.5}Cs_{2.5}PMo_{12}O_{40}$), $H_2O_2$/Mo$(CO)_6$, TBHP/heteropolyacid ($H_3PMo_{12}O_{40}$, $H_3PW_{12}O_{40}$, $H_{0.5}Cs_{2.5}PMo_{12}O_{40}$), TBHP/Mo$(CO)_6$, TBHP/M(acac)$_2$ (M=Mo and V), $H_2O_2$/metal naphthenates (M=Mo, V, Cr, Mn, Ti, Co, Fe, Ni, Ta, Re, Nb, Ri, Re, Rh and W), TBHP/$VOC_2O_4$, TBHP/$M^1_2M^{IV}O(C_2O_4)_2$, TBHP/$M^1_2M^{IV}O(C_2O_4)_3$, TBHP/$M^1_2M^{IV}O_2(C_2O_4)_2$, $H_2O_2$/metal octoate (M=Mo, V, Co, Fe, Ni, Ti, Cr, Mn, W, Ce, Ru), TBHP/metal octoate (M=Mo, V, Co, Fe, Ni, Ti, Cr, Mn, W, Ce and Ru) or a mixture thereof.

Preferable examples of an oxidant herein are an $O_2/CO_2$ mixture, TBHP, $H_2O_2$, t-butylhydroperoxide (TBHP), $H_2O_2/HCOOH$, $H_2O_2/CF_3COOH$, ethylbenzene hydroperoxide, cumyl hydroperoxide and cyclohexylperoxodicarbonate $((C_6H_{11})_2C_2O_6)$.

In particular, an $O_2/CO_2$ mixture is most preferred as an oxidant in the present invention. Preferably, the $O_2/CO_2$ mixture contains 5-100 vol %, more preferably 7-80 vol %, most preferably 10-60 vol % of $CO_2$.

Further, the $O_2/CO_2$ mixture may comprise 5-30 vol % of helium or argon, whereas nitrogen is preferred to be contained in the amount of less than 20 vol %, more preferably less than 10 vol %, most preferably less than 5 vol % and ultimately 0%, because a large amount of nitrogen may lead the oxidation in an undesired direction.

When used in combination with an $O_2/CO_2$ or an $O_2/CO_2/Ar(N_2)$ oxidant, a homogeneous catalyst herein produces intermediate active species such as peroxide, hydroperoxide and peroxocarbonate in situ in a reactor. As illustrated below, these active species function as an oxidant, thus replacing expensive conventional oxidants.

Scheme 4: A speculative trend in reactivity for oxidation using TBHP in the oxirane blue Mo-solution catalyst

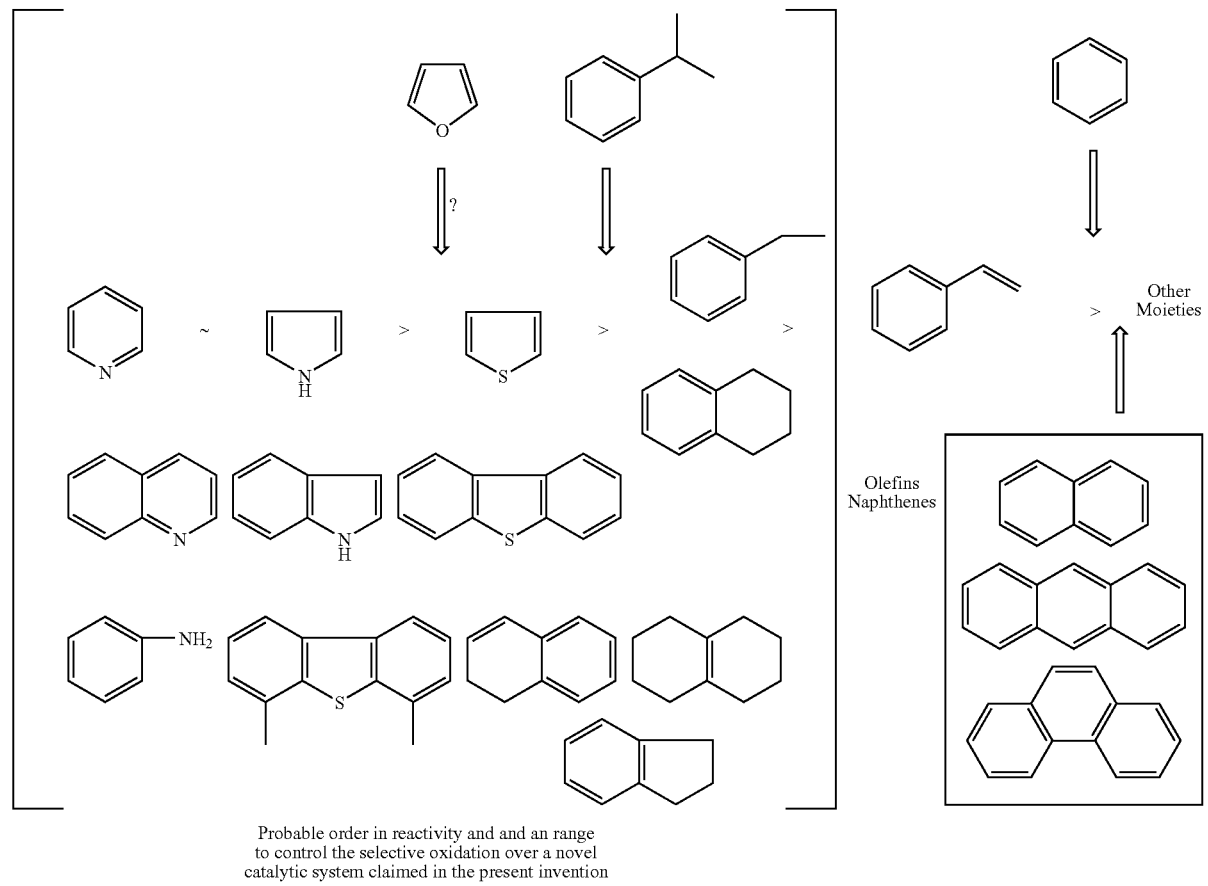

Probable order in reactivity and and an range to control the selective oxidation over a novel catalytic system claimed in the present invention A process herein may remarkably produces a sulfur- or nitrogen-containing compound, and also produce oxygenates useful in enhancing a cetane number or an octane number. Therefore, as used herein, the term "hydrocarbon substrate" includes any hydrocarbon that comprises a sulfur- or a nitrogen-containing compound to be removed and that needs the production of oxygenates.

Examples of hydrocarbon substrate herein include but are not limited to the compounds in Table 3.

TABLE 3

(a) FCC product selected from the group consisting of gasoline, light cycle naphtha (LCN), heavy cycle naphtha (HCN), heavy oil fraction (middle distillate), light cycle oil (LCD), heavy cycle oil (HCO) and clarified oil (CLO)
(b) hydrogenated (HDS or HDN) counterparts of (a) the FCC products
(c) heavy oil, bunker C oil or atmospheric and vacuum distilled resid bottoms
(d) asphaltene separated from crude oil
(e) long crude oil
(f) tar sand, oil sand
(g) hydrogenated liquefied coal or H-coal
(h) chemically cleaned coal that has undergone de-ashing, desulfurizing and denitrogenating processes
(i) cokes, graphite or shale oil Preferable examples of hydrocarbon substrate herein include without limitation (a) a reformulated gasoline that has undergone desulfurization and denitrogenation through a hydrogenation process, followed by a selective oxidation for increasing the amount of oxygenates; (b) a light cycle oil, a heavy cycle oil, a heavy oil fraction or a mixture thereof that has undergone a hydrogenation; and (c) a reformulated diesel that has undergone desulfurization and denitrogenation through a hydrogenation process, followed by a selective oxidation for increasing the amount of oxygenates.

Among them, a process herein may also be applied to transportation fuel, and even to a gasoline or a diesel that has undergone the conventional HDS process. Consequently, no additional process, e.g., cracking reaction and blending procedure with special oxygenates is not required to restore the desired physical and chemical properties such as octane or cetane number in the case of gasoline and to meet the oxygen content (2.0-2.5 wt % of oxygen) required by the reformulated gasoline and the future oxygenated diesel, respectively.

As used herein, the term "benzylic or allylic compound" includes any benzylic or allylic compound that may be oxidized into oxygenates, which may serve as an octane booster in the reformulated gasoline and a cetane booster for the future oxygenated diesel. Examples of such compound include without limitation tetralin or alkyltetralin derivative; partially hydrogenated naphthalene or naphthene; alkylbenzene derivatives such as xylene, cumene, isopropylbenzene, mesitylene, psuedocuemene and durene; and a mixture thereof.

As used herein, the term "oxygenate" includes any compounds that may increase a cetane number or an octane number of a hydrocarbon substrate herein. Examples of such compound include without limitation alcohols such as α-tetralol and 1-(2-naphthyl)ethanol; ketones such as Q-tetralone, 1,4-naphthoquinone and fluorenone; aldehydes such as Q-tetralene aldehyde; organic acid esters such as methyloleate, propyl linoleate, butylstearate and aromatic or aliphatic organic acids such as dibutyl meleate, terephthalic acid, 2,6-naphthalenedicarboxylic acid and stearic acid; ethers such as glyme, diglyme, triglyme and tripropylene glycol methyl ether; and a mixture thereof.

As used herein, the term "sulfur-containing compound" refers to any sulfur-containing compound existing in a hydrocarbon substrate herein. Examples of such compound include without limitation dialkyldibenzothiophene (4,6-DMDBT or 2,5-DMDBT), 4-alkyldibenzothiophene (4-MDBT), dibenzothiophene (DBT), alkylbenzothiophene, benzothiophene (BT), dialkylthiophene, thiophene, diphenyl sulfide, thiophenol, methylphenyl sulfide, alkyl disulfide and a mixture thereof.

As used herein, the term "sulfur-containing precursor" refers to any oxygen-containing compounds, into which a sulfur-containing compound herein is oxidized. Examples of such compound include without limitation sulfoxides or sulfones of a sulfur-containing compound herein.

As used herein, the term "nitrogen-containing compound" refers to any nitrogen-containing compounds existing in a hydrocarbon substrate herein. Examples of such compound include without limitation pyridine, quinoline, pyrrole, indole, carbazole, and alkyl derivative thereof, aromatic and aliphatic amines and a mixture thereof.

As used herein, the term "nitrogen-containing precursor" refers to any oxygen-containing compounds, into which a nitrogen-containing compound herein is oxidized. Examples of such compound include without limitation N-oxides, oximes, nitrobenzenes, nitrosobenzenes and indigos of a nitrogen-containing compound herein.

As used herein, the term "biphasic system" refers to any nonpolar or polar system. Examples of such system include without limitation oil/acetonitrile, oil/DMF, oil/acetic acid, oil/pyrrolidone, oil/NaOH aqueous solution, oil/NaHCO$_3$ aqueous solution, oil/Na$_2$CO$_3$ aqueous solution, oil/acetic acid-water mixture, oil/t-BuOH, oil/MeOH and oil/MeCN.

As used herein, the term "oil" mainly refers to a hydrocarbon substrate (e.g. TGO) to which a process herein may be applied in a commercial or industrial way. However, the term "oil" herein includes nonpolar solvents such as benzene and n-octane that may be used as a synthetic model substrate.

For such a biphasic system, an "oxidant" or an "oxidation system of homogeneous catalyst-oxidant" may be selected among $O_2$(10-40%)-$CO_2$/heteropolyacid, $O_2$(10-40%)-$CO_2$/Mo$^{6+}$ (blue oxirane catalyst solution), $O_2$(10-40%)-$CO_2$/Mo$^{6+}$-M$^{n+}$ catalyst solution (M=Fe, Co, Ru, Cu, Zr, Hf, Ni and Zn), hydroperoxide/heteropolyacid, hydrotalcite and hydrotalcite-like materials.

In particular, for a biphasic system of a non-MC-type catalyst, an oxidant is preferred to be selected among peroxy organic acid such as an $O_2$/$CO_2$ mixture, TBHP, $H_2O_2$, HCOOOH and $CH_3COOOH$; or ethylbenzene hydroperoxide, cumylhydroperoxide, cyclohexyl peroxodicarbonate ($C_6H_{11})_2C_2O_6$). Most preferably, an oxidant in a biphasic system of a non-MC-type catalyst is selected among an $O_2$/$CO_2$ mixture, $H_2O_2$, TBHP, HCOOOH, $CH_3COOOH$, and most preferably the oxidant is an $O_2$/$CO_2$ mixture.

A selective oxidation is preferred to be conducted at 1-30 atm, more preferably at 5-20 atm and the most preferably at 10-15 atm. When the reaction pressure is outside the aforementioned ranges, the reaction may not proceed completely or a safety issue may occur. The oxidation temperature is preferably within the range of 80-210° C., more preferably between 130-190° C. and the most preferably between 140-180° C. When the temperature is outside the ranges, oxidation may proceed incompletely or excessively.

Sulfur- or nitrogen-containing compounds may be removed by means of various post-treatment such as filtration, fractionation, selective adsorption, solvent extraction, catalytic destruction, selective oxidation, pyrolysis and a combination thereof.

The filtration may be conducted by removing or separating sulfur- or nitrogen-containing precursors, which are produced during the selective oxidation and precipitated in a polar solvent layer by a filtration or a centrifugation.

The selective adsorption may be conducted by using one or more adsorbent selected among activated carbon fiber, carbon nanotube, carbon molecular sieve; M/activated carbon fiber, M/carbon nanotube, M/carbon molecular sieve (M=Pd, Zn, Cu, Ni, Fe, Mn, Ti, Mg, Sr, Ba, Na, K); mesoporous alumina, silica gel, zeolite; metal-activated mesoporous alumina, metal-activated silica gel, metal-activated zeolite; M/Al$_2$O$_3$, SiO$_2$, MCM-41 (M=Y, La, Ni, Mo, Cr, W, V, Co, Cu), Perovskite, Y$^{3+}$-stabilized metal oxide; ZrO$_2$, CeO$_2$—ZrO$_2$ and PrO$_2$—ZrO$_2$; solid solutions such as MgO—MgAl$_2$O$_4$, MgAl$_2$O$_4$.xMgO and MgAl$_2$O$_4$.yAl$_2$O$_3$; Cs/ZSM-5, Cs/SiO$_2$, Ba/MCM-41, Zn—Al double layered hydroxide (DLH), hydrotalcite, AlGaPON, ZrGaPON, Mg$_{0.819}$Ga$_{0.181}$(OH)$_2$(CO$_3$).

The solvent extraction may be conducted by using one or more solvent selected from N,N'-dimethyl formamide (DMF), CH$_3$CN, DMSO, MeOH, t-BuOH, methyl ethyl ketone (MEK), CH$_3$COOH and CX$_3$COOH, dimethylpyrrolidone, dioxane, sulfolane, alkaline metal and an aqueous sodium carbonate (NaHCO$_3$, Na$_2$CO$_3$) solution.

The catalytic destruction may be conducted in the presence of one or more base catalyst selected from t-BuONa, NaOH, NaOH—KOH, CH$_3$CO$_2$Na, Li$_2$CO$_3$—NaCO$_3$—K$_2$CO$_3$ eutectic mixture, Raney Ni, Raney Fe, Na/K, Na/Al$_2$O$_3$, K/Al$_2$O$_3$, Li/MgO, Cs/SiO$_2$, MgFe$_2$O$_4$, [Ni(COD)$_2$Bipy], commercial HDS catalyst, commercial HDN catalyst, hydrotalcite, Ce/V/MgO.MgAl$_2$O$_4$, MgO.MgAl$_2$O$_4$ solid solution and Zn—Al double-layered hydroxides.

The pyrolysis may be applied to dihydronaphthalene, tetralin, decaline, hydrogenated LCN, LCO and HCO, and may be conducted in the presence of one or more base catalyst selected from the H-donor solvent and/or MgO.MgAl$_2$O$_4$, xAl$_2$O$_3$.yMgAl$_2$O$_4$ solid solution, Cs/ZSM-5, Ba/MCM-41, Cs/SiO$_2$, Zn—Al double-layered hydroxide, hydrotalcite and hydrotalcite-like materials, Li/MgO, Li/MgO—CaO, Na/Al$_2$O$_3$, K/Al$_2$O$_3$, AlGaPON, ZrGaPON and Mg$_{1-x}$Ga$_x$(OH)$_2$CO$_3$.

Various kinds of wasted catalysts such as a spent FCC catalyst, a spent RFCC catalyst, a zeolite (ZSM-5, MCM-41, etc.), a commercial HDS catalyst and a commercial HDN catalyst may be recycled and used as the MgO.MgAl$_2$O$_4$, the xAl$_2$O$_3$.yMgAl$_2$O$_4$ solid solution, the Ce/V/MgO.MgAl$_2$O$_4$, (commercial DeSOx catalyst), the Cs/ZSM-5, the Na/Al$_2$O$_3$, the K/Al$_2$O$_3$, the Cs/SiO$_2$, the Ba/MCM-41, NaOH—KOH, NaOH, CVD Fe/Mo/DBH, and FCC catalyst.

In the present invention, the desulfurization is preferred to be conducted to such a level that sulfur-containing compounds may be removed less than 20 ppm, more preferably less than 10 ppm, the most preferably less than 5 ppm, and ultimately 0 ppm.

Preferably, the desnitrogenation is also conducted to such a level that nitrogen-containing compounds may be removed less than 10 ppm, preferably less than 5 ppm, most preferably less than 2.5 ppm, and ultimately 0 ppm.

Further, the extent of oxidizing the benzylic and allylic hydrocarbons can be determined by the oxygen content stipulated for the current and future transportation fuels, e.g., the requirements for the octane number of the reformulated gasoline and the cetane number for the future oxygenated diesel, the level of the benzylic hydrocarbon existing in the feed substrate and other environmental regulations on the oxygen content. Preferable content of oxygenates is 2.0-5.0 wt %, more preferably 2.2-3.0 wt %, most preferably 2.2-2.7 wt % on the basis of oxygen.

EXAMPLES

Figure 1:
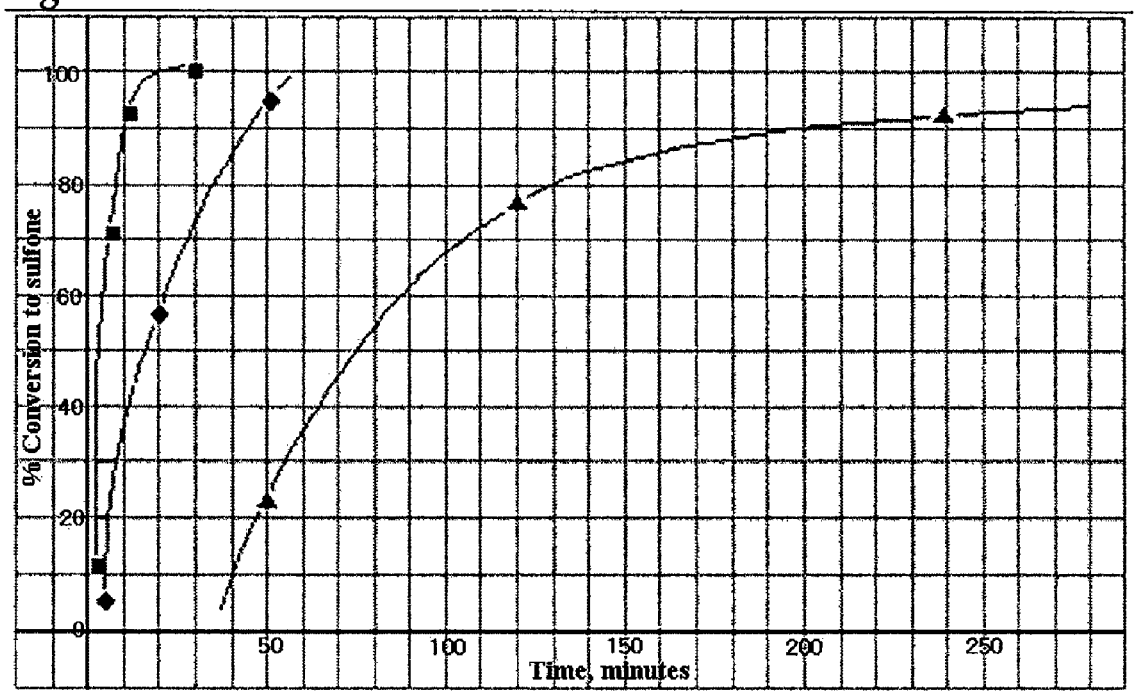
FIG. 1 shows time-dependency of degree of oxidation conducted by using Mo(oxirane) catalyst solution and TBHP (□: 4,6-DMDBT, o: DBT, Δ: BT).

The present invention is described more specifically by the following Examples. Examples herein are meant to illustrate the present invention only, but they should not be construed as limiting the scope of the claimed invention.

Example 1

(1) Preparation of "Mono-Phasic" Selective Oxidation System of "Mono-Metal Homogeneous Catalyst"+"TBHP Oxidant"

A homogeneous catalyst solution was prepared as follows. S-, N-compounds and benzylic hydrocarbons such as tetralin contained in hydrotreated LCN, HCN, LCO, HCO and clarified oil may be selectively oxidized in a reactor by using the homogeneous catalyst solution.

A homogeneous catalyst was prepared by using M-complex salts dissolved in hydrocarbons such as M-naphthenate, M-stearate, $M(CO)_6$, $MO_2(acac)_2$ (acac: acetylacetonate), M-octoate (M: Mo, V, Te, Re, Ta, Nb) or by reacting nonsoluble precursors such as various metal powders (e.g. Mo, V, Te, Re, Ta and Nb), $MoO_3$ and molybdic acid with TBHP contained in t-butyl alcohol (TBA).

In particular, Mo(oxirane) homogeneous catalyst has a relatively high selectively oxidative activity, and 1,000 mL of blue catalyst solution was prepared by dissolving 1.48 g of Mo powders (<200 mesh size) in a mixed solvent of TBHP:TBA:ethylene:glycol (2:4:1 weight ratio). Addition of small amount of formic acid, t-butyl formate or t-butyl acetate facilitated the preparation of the catalyst solution.

To further improve economical efficiency, a used solution, discharged during the commercial process of manufacture of propylene oxide, may be used instead of this mixed solvent. This homogeneous oxirane blue Mo-catalyst solution may be recovered by treating the spent catalyst solution with a basic aqueous solution containing 1% NaOH or $NH_4OH$, followed by separating the resulting aqueous and organic phases and precipitating the aqueous solution with a base such as CaO.

(2) Selectively Oxidative Activity of "Mono-Phasic" Selective Oxidation System of "Mono-Metal Homogeneous Catalyst"+"TBHP Oxidant"

Liquid-phase oxidation was conducted by using thus prepared mono-metal catalyst containing various metals as shown in Table 4 in benzene solvent at 80° C. for 2 hours. The selectively oxidative activity was observed, and the results are presented in Table 4.

| Substrate mixture | |
|---|---|
| Diethyl sulfide | $\frac{1}{3} \times 10^{-2}$ mole |
| Benzothiophene | $1.3 \times 10^{-2}$ mole |
| t-BuOOH (TBHP) | 0.03 mole |
| Benzene | 52 mL |
| Mo(oxirane) catalyst solution | 0.100 g (100 ppm Mo) |

TABLE 4

| Catalyst | Et$_2$S Sulfoxide | Et$_2$S Sulfone | BT Sulfone | DBT Sulfoxide | DBT Sulfone | % TBHP in product |
|---|---|---|---|---|---|---|
| Blue Mo Solution* | 0 | 100 | 80 | 0 | 100 | 2.28 |
| MoO$_2$(acac)$_2$ | 0 | 100 | 91 | 0 | 100 | 1.60 |
| VO(acac)$_2$ | 0 | 100 | 0 | 25 | 32 | 0.30 |
| VO-phthalocyanine | 0 | 95 | 0 | 16 | 22 | 3.37 |
| Cr(acac)$_3$ | 11 | 89 | 0 | 39 | 9 | 1.69 |
| Ti(acac)$_4$ | 0 | 96 | 0 | 25 | 8 | 4.10 |
| Zr(acac)$_4$ | 0 | 92 | 0 | 0 | 0 | 4.25 |
| Hf(acac)$_4$ | 12 | 81 | 0 | 0 | 0 | 4.38 |
| Ta(OC$_6$H$_5$)$_6$ | 90 | 7 | 0 | 0 | 0 | 4.90 |
| Ce(acac)$_3$ | 88 | 6 | 0 | 0 | 0 | 3.82 |
| Fe(acac)$_3$ | 95 | 0 | 0 | 0 | 0 | 4.90 |
| Mn(acac)$_3$ | 95 | 0 | 0 | 0 | 0 | 4.51 |
| Co(acac)$_2$ | 94 | 0 | 0 | 0 | 0 | 4.98 |
| Mg(acac)$_2$ | 93 | 0 | 0 | 0 | 0 | 4.78 |
| Cu(acac)$_2$ | 91 | 0 | 0 | 0 | 0 | 4.26 |
| Ni(acac)$_2$ | 91 | 0 | 0 | 0 | 0 | 4.86 |
| Zn(acac)$_2$ | 89 | 0 | 0 | 0 | 0 | 4.96 |
| Al(acac)$_3$ | 89 | 0 | 0 | 0 | 0 | 4.93 |

*Blue Mo(oxirane) catalyst solution prepared by using Mo metal powders (3) Selectively Oxidative Activity of "Mono-Phasic" Selective Oxidation System of "Mono-Metal Homogeneous Catalyst"+"Other Oxidant than TBHP"

Selective oxidation system of "homogeneous catalyst"+"other oxidant than TBHP" was prepared by using Mo-catalyst solution and/or V-catalyst solution, which showed superior catalytic activity, as a catalyst, and pseudocumene hydroperoxide, ethylbenzene hydroperoxide, $H_2O_2$/HCOOH, $H_2O_2$/$CH_3COOH$ and/or $CX_3COOH$ (X=F, Cl) as an oxidant instead of TBHP. Oxidative activity (conversion and oxidative selectivity) was ascertained to be equivalent to that of TBHP.

The economics of the process may be improved by directly preparing the high-priced oxidants in a reactor according to any known method instead of using already synthesized hydroperoxide, peroxide, $H_2O_2$ or peracids. For example, $H_2O_2$ was directly generated by feeding $H_2$ and $O_2$ over Pt(0.1%)-Pd(1%)/TS-1 [P. Albert et al., J. Mol. Catal. 58, 115 (1990); R. Meiers et al., Catal. Lett., 59, 161 (1999)] or Pd catalyst [Kirch-Othmer Encyclopedia of Chem. Tech., 13, 4th Ed., 1995, p. 961] or Pt—Au catalyst or zeolite catalyst such as MFI-structured TS-1 or MEL-structured TS-2 in situ in the reactor containing water, $H_2O$+MeOH, acetone and/or $CH_3CN$ as a solvent. The generated $H_2O_2$ was utilized for the oxidation, thereby increasing the economical efficiency of the total process [B. Notari et al., Advances in Catalysis, Vol 41, p. 253, 1996, Academic Press; R. N. Cochran et al., U.S. Pat. No. 5,039,508 (1991)].

Selective oxidation was also conducted by using an $O_2/CO_2$ mixture (a premixed gas of $O_2$ and $CO_2$ in a predetermined mixing ratio) as an oxidant gas instead of the high-priced oxidants together with the mono-metal Mo- and/or V-catalyst solution. As a result, a peroxocarbonate, i.e., an active intermediate species in-situ generated, was ascertained to increase the selectivity and the conversion to DBT sulfone. The yield of DBT sulfone was increased as high as to be equivalent to or even superior to the case of TBHP by conducting selective oxidation at 5-15 atm using an autoclave.

Example 2

(1) Preparation of "Mono-Phasic" Selective Oxidation System of "Binary Homogeneous Catalyst"+"TBHP Oxidant"

Various selective oxidation systems of "binary homogeneous catalyst"+"TBHP oxidant" was prepared by incorporating a secondary metal compound, in particular a metal and/or an organometal compound that may promotes the selective oxidation of allylic and benzylic hydrocarbon as shown in Table 4, into the blue Mo(oxirane) catalyst prepared by dissolving Mo powders in TBA/TBHP (2) Selectively Oxidative Activity of "Mono-Phasic" Selective Oxidation System of "Binary Homogeneous Catalyst"+"TBHP Oxidant"

Selective oxidation of DBT was conducted by using thus prepared selective oxidation system of "binary homogeneous catalyst"+"TBHP oxidant" at 80° C. and under atmospheric pressure for 2 hours, and the results are presented in Table 5.

TABLE 5

| No. | Catalyst | % TBHP | DBT sulfone |
|---|---|---|---|
| 1. | Mo(oxirane)-Co(acac)$_2$ [TBA/TBHP] [benzene] | 3.65 | (−)* |
| 2. | Mo(oxirane)-Mn(acac)$_3$ [TBA/TBHP] [benzene] | 4.06 | (−)* |
| 3. | Mo(oxirane)-Co-octoate [TBA/TBHP] [aqueous solution] | 3.02 | (+)** |
| 4. | Mo(oxirane)-Co(acac)$_2$ [TBA/TBHP] [aqueous solution] | 3.65 | (+)** |
| 5. | Mo(CO)$_6$—Co(acac)$_2$ [TBA] [TBA] | 1.07 | (+)** |
| 6. | Mo(oxirane)-Cu-phthalocyanine | 2.21 | (+)** |
| 7. | Mo-M | 3.01 | (++)*** |

M: Co, Mn, Cu, Fe, Rh, Re, Nb
Powders are dissolvedn in TBA/TBHP
*Sulfone undetectable
**Sulfone detectable
***Large amount of sulfone detectable The deactivation of Mo-catalyst, as shown in Table 5, is attributed to the fact that both Co and Mo separated completely as a sticky brown suspension from a benzene solution of Co(acac)$_3$ blended with the blue Mo-oxirane solution (run 1). The blue nanoparticles of Mo precipitates separated out of the blue solution from the beginning. The sticky brown suspension was adsorbed onto nanoparticles of the original blue Mo precipitates, and thus the Mo-center was completely covered by Co, and consequently denied the Mo-center from the surface access to the sulfur sites.

Similar effect was also observed with Mn(acac)$_3$ case (run 2). The original blue Mo-nanoparticles precipitated from the blue Mo-oxirane solution was quite active for the sulfoxidation in the absence the second metals (Co, Mn).

On the contrary, the binary catalyst system became very effective for the suloxidation as well as benzylic carbon oxidation as long as the second metal remained independently in a discrete metal ion in a homogeneous phase without strong mutual interaction (run 3-7). In particular, a binary catalyst system prepared by two kinds of metal powders in TBA/TBHP showed superior catalytic activity, being very useful in preparation of DBT sulfone (run 7).

(3) Preparation of "Mono-Phasic" Selective Oxidation System of "Binary Homogeneous Catalyst"+"Other Oxidant than TBHP" and its Selectively Oxidative Activity A binary selective oxidation system was prepared by using an $O_2/CO_2(30/70)$ mixed oxidant instead of TBHP. Selective oxidation was conducted in an autoclave at 5-15 atm by using the binary selective oxidation. As a result, the production of DBT sulfone in remarkably high yield was ascertained without using hydroperoxides such as TBHP.

Further, selective oxidation of benzylic hydrocarbons such as tetralin was also conducted. Cetane boosters such as ketones (e.g., tetralone), alcohols and aldehydes were ascertained to be produced in a relatively high yield.

Example 3

Each of refractory thiophenes such as DBT, 4-MDBT and 4,6-DMDBT was dissolved in Mo(oxirane) catalyst solution and oxidized with TBHP. The time dependency of degree of oxidation was observed, and the results are presented in FIG. 1 (□: 4,6-DMDBT, o: DBT, Δ: BT).

FIG. 1 shows that the reactivity trend of the refractory sulfur compounds toward the selective sulfoxidation process become exactly opposite to that observed in the conventional HDS reaction. The most refractory sulfur compound, 4,6-

DMDBT, which is stable at an elevated temperature (650° C.) and resistant to desulfurization even under the extreme conditions of the HDS process, becomes the easiest substrates for the selective oxidative.

These results explicitly show that S-free or deep or ultra-deep desulfurization may be achieved according to the present invention such as TGO, thereby overcoming the technical problems in the conventional HDS process.

Example 4

(1) Preparation of "Biphasic" Selective Oxidation System of "Binary Homogeneous Catalyst"+"TBHP Oxidant" and its Selectively Oxidative Activity Against "Sulfur-Containing Compounds"

Catalyst solution (2.5 μmol Mo+2.5 μmol W) prepared by dissolving Mo and W metal powders (<200 mesh) in a mixed solvent of TBHP:TBA:EG (2:4:1) was mixed with 50 mL of $CH_3CN$. Biphasic mixture was prepared by adding thus obtained $CH_3CN$ solution to n-octane solution containing 10 mmol of DBT and 10 mmol of 4,6-DMDBT.

Selective oxidation was conducted by using thus obtained biphasic reaction system along with TBHP as an oxidant at 60° C. with violent agitation. During the selective oxidation, the amount of two substrates that moved from the octane phase to the $CH_3CN$ layer was measured with HPLC. Further, the amount and the rate were also measured without conducting the selective oxidation.

As a result, during the selective oxidation, 99% and 100% of $DBTO_2$ (sulfone) and $4,6\text{-}DMDBTO_2$ (sulfone) were ascertained to rapidly move from the octane phase to the $CH_3CN$ layer, respectively. Meanwhile, without selective oxidation, 65% of DBT and 56% of 4,6-DMDBT moved to the $CH_3CN$ layer, respectively.

These results show that a significant level of S-removal may be attained without conducting oxidation while deep or ultra-deep desulfurization still requires selective oxidation. In this case, a biphasic solvent system is very useful in that refractory thiophenes may be quantitatively removed in a biphasic solvent system.

Further, it was ascertained that reaction results such as selectivity and yield may be controlled by the modification of the biphasic system, for example, by appropriately selecting solvents. It was also ascertained that, in a certain hydrocarbon substrate, a biphasic selective oxidation system is superior to a mono-phasic system in desulfurization, denitrogenation and/or production of oxygenates.

(2) Preparation of "Biphasic" Selective Oxidation System of "Binary Homogeneous Catalyst"+"TBHP Oxidant" and its Selectively Oxidative Activity Against "Nitrogen-Containing Compounds" and "Allylic or Benzylic Hydrocarbons"

Besides the sulfur-containing compounds, nitrogen-containing compounds and allylic or benzylic hydrocarbon were also subject to selective oxidation by using thus obtained biphasic selective oxidation system. As a result, excellent desulfurization was ascertained and it was also observed that each of the aforementioned compounds were selectively oxidized into corresponding oxygenates.

(3) Preparation of "Biphasic" Selective Oxidation System of "Binary Homogeneous Catalyst"+"Other Oxidant than TBHP" and Its Selectively Oxidative Activity Selective oxidation of biphasic selective oxidation system was conducted by using $H_2O_2$ or $O_2(20\text{-}40\%)/CO_2$(balance) instead of TBHP oxidant. In particular, in the case of $O_2$(20-40%)/$CO_2$(balance), selective oxidation was conducted at 5-15 atm by using an autoclave.

Sulfur- or nitrogen-containing compounds and allylic or benzylic compounds were selectively oxidized in an excellent yield. It was also observed that the produced oxygenates moved to polar solvent layer, thus facilitating the separation or removal of the oxygenates.

Example 5

(1) In-Situ Preparation of "Active Oxygen Oxidant"

A cut in the boiling range of 205-232° C. from hydrotreated HDS fuel oil was analyzed to contain 43.8% paraffin, 36.3% cycloparaffins, 10.1% alkylbenzene and 5.5% tetralin. Among these, alkylbenzene and tetralin are representative benzylic hydrocarbons that exist in various hydrotreated oil fractions.

An attempt to directly generate oxidants and to utilize them as an in-situ oxidant was made by using Co-catalyst solution. Selective oxidation was conducted under the oxygen pressure, 1000 mmHg at 120° C. for 1 hour, and the results are summarized in Table 6.

TABLE 6

| Entry | Co catal. conc. ppm | $O_2$ uptake flow rate [rate/100 g · feed/hr] | Active O % in product | Selectivity % |
|---|---|---|---|---|
| 1 | 200 | 2.04 g | 0.055 | 5.5 |
| 2 | 50 | 2.12 | 0.400 | 38.5 |
| 3 | 20 | 1.15 | 0.345 | 60.5 |
| 4 | 5 | 0.42 | — | — |
| 5 | 30 | 4.59 | 3.88* | |

*In a lower layer separated after selective oxidation at 120° C. for 4 hours (2) Selectively Oxidative Activity of "Active Oxygen Oxidant"

Selective oxidation of DBT was conducted by using Mo-solution (blue oxirane) catalyst and active oxygen in-situ generated in Example 5 under the conditions of Example 5, where the generation of significant amount of active oxygen was ascertained. The selective oxidation was conducted in a liquid phase at 60° C. and under an atmospheric pressure. Within one hour, remarkably high conversion (>95%) of DBTO (sulfoxide) and $DBTO_2$(sulfone) were observed. Besides the Mo-solution catalyst, other V-, Ti-, W-, Re-solution catalysts also showed excellent yield.

In the absence of a transition metal catalyst, the organic hydroperoxide is a weak oxidizing agent and oxidizes sulfides soley to sulfoxides. Even an excess of the hydroperoxide does not lead to the formation of sulfones. However, in the presence of Mo, V, Ti, W and Re, the sulfoxides were ascertained to be quantitatively converted to the corresponding sulfones.

(3) Selectively Oxidative Activity of "Other Oxidant than Active Oxygen" (Air-Oxidation in the Presence Alkali Material In addition to transition metal catalysts, it was ascertained that oxidation of sulfoxide to sulfone by organic hydroperoxides or peroxides occurred in non-aqueous media. For example, dimethylsulfoxide was oxidized in ethanol with cumene hydroperoxide to its sulfone in the presence of NaOH at room temperature. Presence of water in the reaction system retards the oxidation of sulfur compounds. The order of efficiency of base catalysts, estimated based on the yield of sulfone, is as follows: t-BuONa>NaOH (NaOH—KOH)>Na$_2$CO$_3$, CH$_3$CO$_2$Na>>Li$_2$CO$_3$—Na$_2$CO$_3$—K$_2$CO$_3$ (eutectic mixture)

Example 6

(1) Selective Oxidation

Liquid-phase selective oxidation of heavy cyclic naphtha (HCN) containing 0.12% S and 45 ppm N was conducted by using an oxirane blue Mo-solution with an O$_2$(26%)/CO$_2$ (74%) mixture at 80° C. for 2 hours.

(2) Post-Treatment: Filtration

The resulting oxidized product was subject to filtration by using a glass filter and an aspirator under a reduced pressure. Less than 25 ppm of sulfur-containing compounds and no nitrogen-containing compound were detected. DBT sulfone and indigo, which is an oxidized product of indole, existed in solid phase, and were easily separated by filtration.

(3) Post-Treatment: HDS

The resulting oxidized product was subjected to the HDS conditions over the conventional commercial HDS catalyst, Ni(6%)-Mo(18%)/γ-Al$_2$O$_3$-MO$_x$, where M=Ti, Zr, B and P. Less than 20 ppm of S-containing compounds and no N-containing compound were detected.

Refractory condensed thiophenes were converted into sulfones by the selective oxidation, and these sulfones were removed more easily than non-oxidized condensed thiophenes, thereby achieving excellent desulfurization along with ultra-deep denitrogenation.

(4) Post-Treatment: Cracking by Using Spent FCC Catalyst

The resulting oxidized product was subject to hydro-cracking and/or normal cracking process by using a spent FCC catalyst loaded with Ni, V and/or Fe. Less than 10 ppm of sulfur-containing compounds and no nitrogen-containing compound were detected.

These results show that remarkable desulfurization (<10 ppm) and denitrogenation (undetectable) may be attained by using catalyst containing large amount of V, Ni and Fe, which has been already spent in FCC and RFCC (resid fluid catalytic cracking).

Example 7

(1) Selective Oxidation by Using Biphasic System of "Peroxophosphotungstate Oxidant" and "Oil/CH$_3$CN"

Deep desulfurization of diesel oil containing relatively low amount of sulfur compounds (~330 ppm) after the treatment of HDS process was conducted by using peroxophosphotungstate (30% H$_2$O$_2$/trungstophosphoric acid (TPA)) in a biphasic phase (oil/acetonitrile) at 60° C. for 3 hours. The results are shown below.

TABLE 7

| Entry | 30% H$_2$O$_2$/tungstophosphoric acid (μmol/mL) | Oil:MeCN (mL/mL) | S(ppm) |
|---|---|---|---|
| 1 | 0 | 50/50 | 281 |
| 2 | 2.5/2.5 | 50/50 | 34 |
| 3 | 2.5/0.5 | 50/100 | 13 |
| 4 | 2.5/0.5 | 50/200 | 5 |

(2) Selective Oxidation by Using Biphasic System of Peroxophosphotungstate Oxidant and "Other Medium than Oil/CH$_3$CN"

Selective oxidation was conducted under the same conditions by using each of oil/MeOH, oil/DMF, oil/acetic acid, oil/pyrrolidone, oil/p-dioxane, benzene/MeOH and oil/NaOH aqueous solution as a biphasic medium instead of oil/CH$_3$CN. Excellent deep desulfurization and denitrogenation was ascertained as in oil/CH$_3$CN.

(3) Selective Oxidation by Using "Other Oxidant than Peroxophosphotungstate" and "Other Medium Than Oil/CH$_3$CN"

Selective oxidation was conducted under the same conditions by using each of the following oxidants instead of peroxophosphotungstate. Other oxidants such as organic peroxide or hydroperoxide/hetropolyacid, Mg—Al layered double hydroxide (hydrotalcite, 'HT'), Rh/Mg$_6$Al$_2$(OH)$_{16}$.4H$_2$O, Zn—Al layered double hydroxide (hydrotalcite-like materials) also exhibited excellent deep desulfurization and denitrogenation. In particular, HT-like materials incorporated with polyoxometalate anions pillars exhibited remarkably excellent results.

TABLE 8

| M(II)/M(III) LDH | | Incorporated polyoxometalate anion pillars |
|---|---|---|
| Mg | Al | [Mo$_7$O$_{24}$]$^{6-}$, [V$_{10}$O$_{26}$]$^{6-}$, [PMo$_6$W$_6$O$_{40}$]$^{5-}$ |
| Zn | Al | [Ta$_6$O$_{18}$(OH)]$^{7-}$, [Nb$_6$O$_{18}$(OH)]$^{7}$, [PMo$_{12}$O$_{40}$]$^{3-}$, [Mo$_7$O$_{24}$]$^{6-}$, [V$_{10}$O$_{26}$]$^{6-}$, [PMo$_6$W$_6$O$_{40}$]$^{5-}$ |
| Zn | Cr | [Ta$_6$O$_{18}$(OH)]$^{7-}$, [Nb$_6$O$_{18}$(OH)]$^{7}$, [PMo$_6$W$_6$O$_{40}$]$^{5-}$ [PMo$_{12}$O$_{40}$]$^{3-}$, [PMo$_6$V$_6$O$_{40}$]$^{5-}$ |
| Cd | Al | [Mo$_7$O$_{24}$]$^{6-}$, [V$_{10}$O$_{26}$]$^{6-}$, [PMo$_{12}$O$_{40}$]$^{3-}$ |
| Co | Al | [PMo$_6$V$_6$O$_{40}$]$^{5-}$, [Mo$_7$O$_{24}$]$^{6-}$, [V$_{10}$O$_{26}$]$^{6-}$ |

(4) Selective Oxidation in "Biphasic" System by Using "Mono-Metal Homogeneous Catalyst" or "Bi-Metal Homogeneous Catalyst" and "O$_2$/CO$_2$ Oxidant"

Mono-metal solution catalyst and bi-metal solution catalyst were prepared by dissolving metal powders in an appropriate solvent as described above. Selective oxidation was conducted by using air and O$_2$(30%)/CO$_2$(70%) oxidant gas under an atmospheric pressure or in a Ti-autoclave (15 atm) in a biphasic system as listed above for 1-4 hours. Excellent deep desulfurization was ascertained.

Example 8

(1) Selective Oxidation of LCO by Using "Mo(Oxirane) Homogeneous Catalyst" and "TBHP Oxidant"

Hydrotreated light cycle oil (LCO) containing 0.07% sulfur and 40 ppm nitrogen was selectively oxidized by using the oxirane blue Mo-solution with t-BuOOH in a 3-neck flask (1 L) under a controlled condition so as to oxidize the S—, and N-moieties, and further to achieve selective oxidation of allylic or benzylic hydrocarbon to produce useful oxygenates to meet the oxygen requirement stipulated for the reformulated gasoline as well as anticipated regulation level in the diesel oil of next-generation (160° C., 3 hours, atmospheric pressure and 150 rpm stirring).

(2) Production of S- or N-Containing Precursors and Oxygenates

The resulting oxidized product was analyzed to be almost 100% of sulfone, and a significant amount of "carbonyl" compounds were ascertained by the IR technique. N-compounds were also converted into the derivatives that may be easily removed.

(3) Post-Treatment: Pyrolysis in the Absence of Catalyst

An aliquot (40 mL) of the product is subjected to pyrolysis in the absence of a base catalyst in H-donor solvent at 450° C. for 3 hours by using a pyrolysis unit.

As shown below, about 92-97% of desulfurization was attained, while the desulfurization was only 83% in the presence of naphthalene, which is not a H-donor solvent.

TABLE 9

| H-donnor | | Desulfurization % pyrolysis w/o cat.* |
|---|---|---|
| 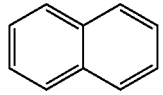 | Naphthalene* | 83 |
| 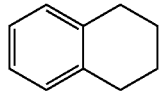 | Tetralin | 97 |
| 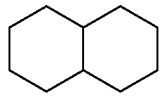 | Decalin | 90 |
| 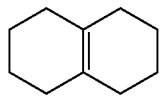 | Octalin | 92 |
| 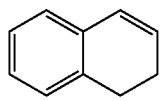 | Dihydronaphthalene | 95 |
| 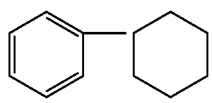 | Cyclohexylbenzene | 94 |

*For comparison (4) Post-Treatment: Pyrolysis in the Presence of Base Catalyst

Another aliquot (40 mL) of the product is subjected to pyrolysis for a comparatively shorter period of time (1 hour) in the presence of a base catalyst (5 g) such as hydrotalcite, $Na/Al_2O_3$, Na/K/active carbon fiber, Cs/ZSM-5, $Cs/SiO_2$ and Ba/MCM-41 in H-donor solvent at 450° C. by using a pyrolysis unit.

As a result, remarkably high degree of desulfurization (>98%) and denitrogenation (100%) was attained. At the same time, the used metals including Mo were also removed at a relatively high level (>95%).

(5) Post-Treatment: Selective Adsorption

Still another aliquot (40 mL) of the oxidized product is filtered to ensure that any solid material, if any, is removed before the filtrate is subjected to the adsorption separation procedure by using active carbon fiber, silica gel and/or carbon molecular sieve (10 mL/g adsorbent). Neither S nor N was detected in the final filtrate.

Other absorbents such as $Pd/Al_2O_3$, $Pt/Al_2O_3$, Pd/active carbon fiber, Pt/active carbon fiber, $PdBaTiO_3$, $Pt/BaTiO_3$, $Pt/Mg_2Al_2O_5$, $Pd/MgAl_2O_4$, $V/Ce/MgAl_2O_4$, $V/Ce/MAl_2O_4$ (M=Fe, Cr, Co, Ni, Cu, Cd, Hg, Zn and Zr), V/Ce/$MgAl_2O_4.xAl_2O_3$, $M/MgAl_2O_4$ (M=Fe, V, Cr, Ta, Nb, Ti, Mo, Zr and Mn), M/zeolite, M/active carbon fiber, M/active carbon fiber, M/carbon molecular sieve, M/carbon nanotube (M=Fe, V, Cr, Ta, Nb, Ti, Mo, Zr and Mn) also showed excellent desulfurization and denitrogenation.

(6) Post-Treatment: Solvent Extraction by Using Polar Solvent

A further aliquot (40 mL) of the oxidized product is filtered, and the filtrate is subjected to selective extraction by using polar solvent such as N,N'-dimethylforamide (DMF), $CH_3CN$ and organic acid.

Amounts of remaining S- and N-components in oxidized product were measured, and compared with those of unoxidized feed. The results below show that excellent desulfurization and denitrogenation was achieved.

TABLE 10

| | S-components (%) | | N-components (%) | |
|---|---|---|---|---|
| Solvent | Unoxidized feed | Oxidized product | Unoxidized feed | Oxidized product |
| DMF | 0.07% | 0.007% | 40 ppm | <3 ppm |

(7) Post-Treatment: Fractionation

Still further aliquot (200 mL) of the oxidized product is filtered, and the filtrate is subject to fractionation. Higher than 90% of desulfurization and ultra-deep denitrogenation (undetectable) was obtained in a fraction obtained by distilling this substrate at the boiling point of the unoxidized substrate.

(8) Analysis of Selectively Oxidized Products

The oxidized products of the hydrotreated LCO was separated into aliphatic, aromatic and polar materials by chromatography, and analyzed by Fourier Transform IR spectroscopy and high performance gas chromatography-mass spectrometry (HPGC-MS).

The analysis shows that aliphatic compounds were mainly paraffins, which remained unoxidized except completely oxidized monocycloalkane, and that aromatic compounds were mainly ketones and lactones. Polar materials were identified as DBT sulfones, oxidized N-compounds such as N-oxide, oxime, indigo, aromatic alcohols, anhydrides, aldehydes, carboxylic acids, esters and ketones such as α-tetralone.

This ascertains that selective oxidation according to the present invention is very useful for desulfurization, denitrogenation and the production of oxygenates, which serve as a cetane or octane booster.

Example 9

Selective Oxidation of Cleaned Coal Followed by Desulfurization (1) Cleaning Raw Coal The bituminous coal was selected as feed coal in this experiment. The coal was pulverized into an appropriate particle size by using a Homoloid hammer mill. The pulverized coal was treated with ash conditioning agent to increase the hydrophilicity on the surface of ash. All these steps were conducted under nitrogen conditions to prevent natural oxidation caused by air.

TABLE 11

Analysis of cleaned coal sample

|  | Ash | Total sulfur | Sulfate | Pyritic | Organic |
|---|---|---|---|---|---|
| Raw coal | 12.7 wt % | 3.30 wt % | 0.32 wt % | 1.96 wt % | 1.02 wt % |
| De-ahsed coal | 7.98 wt % | 1.29 wt % | 0.01 wt % | 0.45 wt % | 0.83 wt % |

(2) Selective Oxidation

Thus obtained de-ashed coal was mixed with distilled water, and a 20 wt % of coal slurry was prepared in a 300 cc stainless steel autoclave, followed by vigorous stirring (~1500 rpm) during the heat treatment. It took 40 minutes to reach reaction temperature (90° C.).

As soon as the reactor system was stabilized at the reactor temperature, a concentrated $Na_2C_2O_4$ solution of sodium oxalate containing $Fe^{3+}$ was pumped into the reactor to immediately generate $[Fe(C_2O_4)_3]^{3-}$ complex catalyst and to adjust the pH of the slurry at 4.0 to 5.5. Some of the $Fe^{3+}$ ions were produced in situ by the reaction of pyrite with an excess amount of oxalate $[C_2O_4]_{2-}$ ions.

A small amount of sample of the aqueous phase was intermittently collected from the reaction via an outlet tube with a metal filter tip to monitor the pH of the system during the run.

Another bituminous coal containing a relatively large amount of organic sulfur was pretreated as described above to obtain a cleaned sample. Selective oxidation was conducted by using the aforementioned sample in the same $Fe^{3+}/[C_2O_4]^{2-}$ media under air and $O_2/CO_2$ condition, followed by base treatment for desulfurization.

Table 12 shows the results of the selective oxidation in the presence of $(Fe^{3+}/[C_2O_4]^{2-}$ (mainly $[Fe(C_2O_4)_3]^{3-}$) catalyst under air $(O_2/N_2)$ and $O_2/CO_2$ conditions, followed by base treatment for desulfurization

TABLE 12

|  | Total S | S type (wt %) | | | S removal | |
|---|---|---|---|---|---|---|
|  | (wt %) | Sulfate | Pyritic | Organic | Pyritic | Organic |
| Feed | 4.02 | 0.02 | 1.86 | 2.14 | — | — |
| Unpromoted | 2.40 | 0.11 | 0.14 | 2.15 | 92% | 0% |
| Promoted (air) | 2.04 | 0.02 | 0.13 | 1.89 | 94% | 12% |
| Promoted ($O_2/CO_2$) | 0.23 | 0 | 0 | 0.23 | 100% | 89% |

An oxidant gas prepared by premixing air ($O_2$ in $N_2$) and $O_2$ (20%) in $CO_2$ (balance) was then introduced, and oxidation was conducted at a constant pressure. When oxygen was introduced to the reactor, a slight increase in temperature was observed. The oxidation was allowed to take place in the pH-controlled buffer medium under vigorous agitation until the desired pyrite ($FeS_2$) removal was attained along with a significant level of organic sulfur removal. If necessary to control the pH of the reaction medium, the sodium oxalate solution was pumped into the reactor during the oxidation.

When the reaction was complete, it was immediately quenched with cold water through the cooling coil. The excess oxygen containing gas in the reactor was released, and the reaction mixture was withdrawn. The coal was separated from the yellow-green filtrate and thoroughly washed with warm water until a test for oxalate in the wash liquors was negative. The coal was dried at 120° C. under high vacuum.

The coal was analyzed for total sulfur, sulfur types, ash carbon, hydrogen, oxygen and nitrogen. The total sulfur was determined by the peroxide bomb method, and sulfur types were analyzed by a modified ASTM method, D2492-68. The ASTM method was followed except that iron determinations were made by atomic absorption spectrophotometry.

(3) Base Treatment for Desulfurization (Base Hydrothermolysis)

A 300 mL monel or inconel autoclave, equipped with an air or an electric motor driven stirrer was used for a reactor. The feed coal, 100×0 mesh size, was depyritized using a promoted oxidation using Na-oxalate promoter. This activated some (with $O_2$ in air) and a significantly high level (with $O_2$ in $CO_2$) of organic sulfur.

The organic sulfur in the coal macerol was oxidized selectively to sulfoxides, sulfones and sulfonates in the promoted oxidation under the aforementioned conditions. The oxidized organic sulfurs, in particular, refractory type sulfurs, along with any remaining pyretic sulfur were removed by the treatment with an aqueous base such as $Na_2CO_3$, NaOH—KOH at an elevated temperature.

The resulting coal product (20 g) was charged in a 300 mL monel autoclave along with 100 mL of an aqueous base solution. The reactor was purged with nitrogen to exclude air. The hydrothermolysis reaction was conducted with vigorous agitation at the following conditions: 125-150° C., 0.5-1.0 hr, water/coal weight ratio of ¾ and $Na_2CO_3$/coal weight ratio of 0.3. Although the base to coal weight ratio generally depends on the organic sulfur activation level, about 2 moles of base are required per mole of sulfur removal.

Table 12 shows that an $O_2/CO_2$ oxidant gas is excellent in desulfurization in the presence of $Fe^{3+}/[C_2O_4]^{2-}$ catalyst, which exists mainly in the form of $[Fe(C_2O_4)_3]^{3-}$. In particular, the removal of organic sulfurs increased from 12% to 89%.

Example 10

Selective Oxidation by Using "Bi-Metal Powders" and "$O_2/CO_2$ Oxidant"

Synthetic model hydrocarbon substrate feeds are prepared as in Table 13 by using a mixture of n-decane (99%, Aldrich), n-hexadecane (99%, Aldrich) and benzene (99%, Aldrich) as a synthetic model oil, and DBT (dibenzothiophene, 98%, Aldrich) and 4,6-DMDBT (4,6-dimethyl dibenzothiophene, 97%, Aldrich) as model compounds.

TABLE 13

| DBT | 5,000 ppm |
|---|---|
| 4,6-DMDBT | 5,000 ppm |
| n-Decane | 34.3 g |
| n-Hexadecane | 34.3 g |
| Benzene | 14.7 g |
| t-Butylbenzene | 14.7 g |

Liquid-phase oxidation was conducted in a 200 mL Ti-autoclave by using thus obtained model substrate and 0.142 g of $FeMoO_4$ powders for 3 hours at 10 atm, 150° C. and 350 rpm while introducing $O_2/CO_2$ (30%/70%).

The resulting oxidized products were analyzed by using GC-MS (Agilent 59731), GC-FID (Agilent 6890N) and PFPD (OI model 5380). The analysis shows that sulfur compounds, i.e., DBT and 4,6-DMDBT, were oxidized to DBT-$O_2$(52%) and 4,6-DMDBT-0(45%), respectively, while no other compounds were oxidized.

In this experiment, it was ascertained that $FeMoO_4$ powders, when uniformly dispersed in a medium, may exhibit a function almost equivalent to that of binary metal (Fe and Mo) homogeneous catalyst as shown in Scheme 5.

That is, the present invention also shows that mono-metal and binary or multi-component homogeneous catalyst may proceed with a solid-liquid phase oxidation via a similar mechanism to that of homogeneous solution catalyst when the solid catalyst are pulverized and uniformly dispersed in an appropriate medium.

When contacted with an $O_2/CO_2$ oxidant gas, even the solid $FeMoO_4$ catalyst converts into a mixture of oxidized products of $Fe_2(MoO_4)_3$ and $Fe_2O_3$ according to the following scheme, thereby showing a catalytic activity analogous to that of a binary homogenous solution catalyst of $Fe^{3+}$ and $Mo^{6+}$ where $Fe_2(MoO_4)_3$ is a main component.

Scheme 5

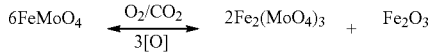

$$6FeMoO_4 \xrightleftharpoons[3[O]]{O_2/CO_2} 2Fe_2(MoO_4)_3 + Fe_2O_3$$

Meanwhile, a remarkable removal of metal contaminants (>89%) was also accompanied by the aforementioned post-treatments besides the desulfurization and the denitrogenation.

Further, it is noteworthy to mention that it was also ascertained that the level of four functions, i.e. desulfurization, denitrogenation, demetallation and production of oxygenates, may be controlled by varying the oxidant/S ratio. This is important in that it is required to modify the oxidation conditions to meet the environmental requirements of near zero S & N and 2.0-2.7% oxygen in the reformulated gasoline as well as future oxygenated diesel.

As described above, a process herein is a non-hydrogen process without causing any increasing cost due to the use of expensive hydrogen unlike in the conventional HDS process. A process herein also accomplishes deep or ultra-deep desulfurization or denitrogenation, and it requires no such complex separation and/or removal process as in the conventional process. Moreover, a process herein also produces useful oxygenates at the same time via a one-pot reaction, without requiring an expensive hydrogenation process.

What is claimed is:

1. A one-pot process for reducing a sulfur- or nitrogen-containing compound and producing an oxygenate in a hydrocarbon substrate, which comprises the steps of:
   (a) placing a homogeneous catalyst in a reactor;
   (b) adding the hydrocarbon substrate in the reactor; and
   (c) introducing an oxidant into the reactor wherein the oxidant is selected from the group consisting of an $O_2/CO_2$ mixture, an $O_2/CO_2/He$ mixture, and $O_2/CO_2/Ar$ mixture, in which the $O_2/CO_2$ mixture comprises 7-80 vol % $CO_2$,
   wherein the homogeneous catalyst is $M^{n+}$/a first solvent or $M^{n+}$/a second solvent/$Mm^+$/a third solvent or a mixture thereof; the $M^{n+}$ is selected from the group consisting of $Co^{3+}$, $Mo^{6+}$, $MoO_2^{2+}$, $MoO_4+$, $MoO_42-$, $V^{5+}$, $VO^{3+}$, $VO_2^{3+}$, $W^{6+}$, $WO_4^{2-}$, $Cr^{3+}$, $Ti^{4+}$, $Fe^{3+}$, $Ni^{2+}$, $Zr^{4+}$, $ZrO^{2+}$, $Hf^{4+}$, $Ta^{6+}$, $Nb^{5+}$, $Ce^{4+}$ and $Ce^{3+}$; the $M_1^{n+}$ is selected from the group consisting of $Co^{3+}$, $Mo^{6+}$, $MoO_2^{2+}$, $MoO^{4+}$ and $MoO_4^{2-}$; the $M_2^{m+}$ is selected from the group consisting of $Co^{3+}$, $Fe^{3+}$, $Ni^{2+}$, $Cu^{2+}$, $V^{5+}$, $VO^{3+}$, $VO_2^{3+}$, $Cr^{3+}$, $Ti^{4+}$, $Zr^{4+}$, $ZrO^{2+}$, $Hf^{4+}$, $Ta^{6+}$, $Nb^{5+}$, $Re^{4+}$, $Ru^{4+}$, $Sm^{4+}$, $Pr^{3+}$ and $Ce^{3+}$;

the first solvent, the second solvent and the third solvent are the same or different and each is independently selected from the group consisting of water, alcohols, $CH_3CN$, DMF, N-pyrrolodone, formic acid, acetic acid, octanoic acid, trifluoroacetic acid, acetic acid-water mixture, aliphatic or aromatic $C_6$-$C_{16}$ hydrocarbon, H-donor solvent, diesel oil, gasoline, LCO, and a mixture thereof.

2. A one-pot process for reducing a sulfur- or nitrogen-containing compound and producing an oxygenate in a hydrocarbon substrate, which comprises:
   (a) converting the sulfur- or the nitrogen-containing compound in the hydrocarbon substrate into a sulfur- or a nitrogen-containing precursor, respectively, and also converting a benzylic or an allylic compound in the hydrocarbon substrate into the oxygenate at the same time via selective oxidation of the hydrocarbon substrate in the presence of a homogeneous catalyst and an oxidant selected from the group consisting of an $O_2/CO_2$ mixture, an $O_2/CO_2/He$ mixture, and $O_2/CO_2/Ar$ mixture, in which the $O_2/CO_2$ mixture comprises 7-80 vol % $CO_2$ at a temperature of 80-210° C. and a pressure of 1-30 atmospheres, and
   (b) conducting a post-treatment selected from the group consisting of filtration, fractionation, selective adsorption, solvent extraction, catalytic destructionselective oxidation, pyrolysis and a combination thereof;
   wherein the homogeneous catalyst is $M^{n+}$/a first solvent or $M^{n+}$/a second solvent/$M^{n+}$/a third solvent or a mixture thereof; the $M^{n+}$ is selected from the group consisting of $Co^{3+}$, $Mo^{6+}$, $MoO_2^{2+}$, $MoO_4+$, $MoO_42-$, $V^{5+}$, $VO^{3+}$, $VO_2^{3+}$, $W^{6+}$, $WO_4^{2-}$, $Cr^{3+}$, $Ti^{4+}$, $Fe^{3+}$, $Ni^{2+}$, $Zr^{4+}$, $ZrO^{2+}$, $Hf^{4+}$, $Ta^{6+}$, $Nb^{5+}$, $Ce^{4+}$ and $Ce^{3+}$; the $M_1^{n+}$ is selected from the group consisting of $Co^{3+}$, $Mo^{6+}$, $MoO_2^{2+}$, $MoO^{4+}$ and $MoO_4^{2-}$; the $M_2^{m+}$ is selected from the group consisting of $Co^{3+}$, $Fe^{3+}$, $Ni^{2+}$, $Cu^{2+}$, $V^{5+}$, $VO^{3+}$, $VO_2^{3+}$, $Cr^{3+}$, $Ti^{4+}$, $Zr^{4+}$, $ZrO^{2+}$, $Hf^{4+}$, $Ta^{6+}$, $Nb^{5+}$, $Re^{4+}$, $Ru^{4+}$, $Sm^{4+}$, $Pr^{3+}$ and $Ce^{3+}$;
   the first solvent, the second solvent and the third solvent are the same or different and each is independently selected from the group consisting of water, alcohols, $CH_3CN$, DMF, N-pyrrolodone, formic acid, acetic acid, octanoic acid, trifluoroacetic acid, acetic acid-water mixture, aliphatic or aromatic $C_6$-$C_{16}$ hydrocarbon, H-donor solvent, diesel oil, gasoline, LCO, and a mixture thereof.

3. The process of claim 2, wherein the $M^{n+}$ and the $M_1^{n+}$ are the same or different and each is independently selected from the group consisting of $Mo^{6+}$, $MoO_2^{2+}$, $MoO^{4+}$, $MoO_4^{2-}$, $V^{5+}$, $VO^{3+}$ and $VO_2^{3+}$.

4. The process of claim 2, wherein the benzylic or allylic compound is selected from the group consisting of tetralin; alkyltetralin derivative; partially hydrogenated naphthalene and naphthene; alkylbenzene derivative selected from the group consisting of xylene, cumene, isopropylbenzene, mesitylene, psuedocuemene and durene; and a mixture thereof;
   the oxygenate is selected from the group consisting of alcohols, ketones, aldehydes, organic acid esters, aromatic or aliphatic organic acids, ethers and a mixture thereof;
   the sulfur-containing compound is selected from the group consisting of dialkyldibenzothiophene (4,6-DMDBT, 2,5-DMDBT), 4-alkyldibenzothiophene (4-MDBT), dibenzothiophene (DBT), alkylbenzothiophene, benzothiophene (BT), dialkylthiophene, thiophene, diphenylsulfide, thiophenol, methylphenylsulfide, alkyldisulfide and a mixture thereof;

the sulfur-containing precursor is a sulfoxide or a sulfone type oxygenate of the sulfur-containing compound;

the nitrogen-containing compound is pyridine, quinoline, pyrrole, indole, carbazole, alkyl derivative thereof, aromatic and aliphatic amines thereof and a mixture thereof; and the nitrogen-containing precursor is a N-oxide, an oxime, a nitron, a nitrosobenzene, a nitrobenzene or an indigo type oxygenate of the nitrogen-containing compound.

5. The process of claim 2, wherein the oxidation is performed at 80-190° C. under 1-20 atm.

6. The process according to claim 2, wherein the sulfur-containing compound and the nitrogen-containing compound are removed to less than 10 ppm and 5 ppm, respectively; and the oxygenate is produced in the amount of higher than 0.5-5 wt % on a basis of oxygen.

7. The process according to claim 2, wherein the hydrocarbon substrate is at least one selected from the group consisting of:
(a) FCC product selected from the group consisting of gasoline, light cycle naphtha (LCN), heavy cycle naphtha (HCN), heavy oil fraction (middle distillate), light cycle oil (LCO), heavy cycle oil (HCO) and clarified oil (CLO);
(b) hydrogenated (HDS or HDN) counterparts of (i) the FCC products;
(c) heavy oil, bunker C oil or atmospheric and vacuum distilled resid bottoms;
(d) asphaltene separated from crude oil;
(e) long crude oil;
(f) tar sand, oil sand or peat;
(g) hydrogenated liquefied coal or H-coal;
(h) chemically cleaned coal that has undergone de-ashing, desulfurizing and denitrogenating processes; and
(i) cokes, graphite or shale oil.

8. The process of claim 7, wherein the hydrocarbon substrate is a coal that has undergone de-ashing and desulfurization of inorganic sulfurs; the homogenous catalyst is $Fe^{3+}/[C_2O_4]^{2-}$; and the oxidant is an $O_2/CO_2$ mixture.

9. The process of claim 2, wherein the hydrocarbon substrate is a transportation fuel selected from the group consisting of:
(a) a reformulated gasoline that has undergone desulfurization and denitrogenation through a hydrogenation process;
(b) a light cycle oil, a heavy cycle oil, a heavy oil fraction or a mixture thereof that has undergone a hydrogenation; and
(c) a reformulated diesel that has undergone desulfurization and denitrogenation through a hydrogenation process.

10. The process of claim 9, wherein the reformulated gasoline or the reformulated diesel has further undergone a selective oxidation for increasing the amount of oxygenates after the hydrogenation process.

11. The process of claim 2, wherein the $O_2/CO_2$ mixture comprises 10-60 vol % of $CO_2$.

12. The process of claim 11, wherein the $O_2/CO_2$ mixture further comprises 5-30 vol % of helium or argon.

13. The process of claim 12, wherein the $O_2/CO_2$ mixture comprises less than 20 vol % of nitrogen.

14. A one-pot process for reducing a sulfur- or nitrogen-containing compound and producing an oxygenate in a hydrocarbon substrate, which comprises:
(a) placing a homogeneous catalyst in a biphasic system;
(b) adding the hydrocarbon substrate in the biphasic system; and
(c) introducing an oxidant into the biphasic system wherein the oxidant is selected from the group consisting of an $O_2/CO_2$ mixture, an $O_2/CO_2$/He mixture, and $O_2/CO_2$/Ar mixture, in which the $O_2/CO_2$ mixture comprises 7-80 vol % $CO_2$, wherein the homogeneous catalyst is $M^{n+}$/a first solvent or $M^{n+}$/a second solvent/$M^{m+}$/a third solvent or a mixture thereof; the $M^{n+}$ is selected from the group consisting of $Co^{3+}$, $Mo^{6+}$, $MoO_2^{2+}$, $MoO_4+$, $MoO_4^{2-}$, $V^{5+}$, $VO^{3+}$, $VO_2^{3+}$, $W^{6+}$, $WO_4^{2-}$, $Cr^{3+}$, $Ti^{4+}$, $Fe^{3+}$, $Ni^{2+}$, $Zr^{4+}$, $ZrO^{2+}$, $Hf^{4+}$, $Ta^{6+}$, $Nb^{5+}$, $Ce^{4+}$ and $Ce^{3+}$; the $M_1^{n+}$ is selected from the group consisting of $Co^{3+}$, $Mo^{6+}$, $MoO_2^{2+}$, $MoO^{4+}$ and $MoO_4^{2+}$; the $M_2^{m+}$ is selected from the group consisting of $Co^{3+}$, $Fe^{3+}$, $Ni^{2+}$, $Cu^{2+}$, $V^{5+}$, $VO^{3+}$, $VO_2^{3+}$, $Cr^{3+}$, $Ti^{4+}$, $Zr^{4+}$, $ZrO^{2+}$, $Hf^{4+}$, $Ta^{6+}$, $Nb^{5+}$, $Re^{4+}$, $Ru^{4+}$, $Sm^{4+}$, $Pr^{3+}$ and $Ce^{3+}$;

the first solvent, the second solvent and the third solvent are the same or different and each is independently selected from the group consisting of water, alcohols, $CH_3CN$, DMF, N-pyrrolodone, formic acid, acetic acid, octanoic acid, trifluoroacetic acid, acetic acid-water mixture, aliphatic or aromatic $C_6$-$C_{16}$ hydrocarbon, H-donor solvent, diesel oil, gasoline, LCO, and a mixture thereof.

15. A one-pot process for reducing a sulfur- or nitrogen-containing compound and producing an oxygenate in a hydrocarbon substrate, which comprises:
(a) converting the sulfur- or the nitrogen-containing compound in the hydrocarbon substrate into a sulfur- or a nitrogen-containing precursor, respectively, and also converting a benzylic or an allylic compound in the hydrocarbon substrate into the oxygenate at the same time via a selective oxidation of the hydrocarbon substrate in a biphasic system comprising a homogeneous catalyst and an oxidant selected from the group consisting of an $O_2/CO_2$ mixture, an $O_2/CO_2$/He mixture, and $O_2/CO_2$/Ar mixture, in which the $O_2/CO_2$ mixture comprises 7-80 vol % $CO_2$ at a temperature of 80-210° C. and a pressure of 1-30 atmospheres, and
(b) removing a layer that comprises the a sulfur- or nitrogen-containing precursor;

wherein the homogeneous catalyst is $M^{n+}$/a first solvent or $M^{n+}$/a second solvent/$M^{m+}$/a third solvent or a mixture thereof; the $M^{n+}$ is selected from the group consisting of $Co^{3+}$, $Mo^{6+}$, $MoO_2^{2+}$, $MoO_4+$, $MoO_4^{2-}$, $V^{5+}$, $VO^{3+}$, $VO_2^{3+}$, $W^{6+}$, $WO_4^{2-}$, $Cr^{3+}$, $Ti^{4+}$, $Fe^{3+}$, $Ni^{2+}$, $Zr^{4+}$, $ZrO^{2+}$, $Hf^{4+}$, $Ta^{6+}$, $Nb^{5+}$, $Ce^{4+}$ and $Ce^{3+}$; the $M_1^{n+}$ is selected from the group consisting of $Co^{3+}$, $Mo^{6+}$, $MoO_2^{2+}$, $MoO^{4+}$ and $MoO_4^{2-}$; the $M_2^{m+}$ is selected from the group consisting of $Co^{3+}$, $Fe^{3+}$, $Ni^{2+}$, $Cu^{2+}$, $V^{5+}$, $VO^{3+}$, $VO_2^{3+}$, $Cr^{3+}$, $Ti^{4+}$, $Zr^{4+}$, $ZrO^{2+}$, $Hf^{4+}$, $Ta^{6+}$, $Nb^{5+}$, $Re^{4+}$, $Ru^{4+}$, $Sm^{4+}$, $Pr^{3+}$ and $Ce^{3+}$;

the first solvent, the second solvent and the third solvent are the same or different and each is independently selected from the group consisting of water, alcohols, $CH_3CN$, DMF, N-pyrrolodone, formic acid, acetic acid, octanoic acid, trifluoroacetic acid, acetic acid-water mixture, aliphatic or aromatic $C_6$-$C_{16}$ hydrocarbon, H-donor solvent, diesel oil, gasoline, LCO, and a mixture thereof.

16. The process of claim 15, wherein the biphasic system is a nonpolar/polar system selected from the group consisting of oil/acetonitrile, oil/DMF, oil/acetic acid, oil/pyrrolidone, oil/NaOH aqueous solution, oil/$NaHCO_3$ aqueous solution, oil/

$Na_2CO_3$ aqueous solution, oil/acetic acid-water mixture, oil/t-BuOH, oil/MeOH and a combination thereof; and the oxidant in the biphasic system is selected from the group consisting of $O_2$(10-40%)-$CO_2$/heteropolyacid, $O_2$(10-40%)-$CO_2$/$Mo^{6+}$(blue oxirane catalyst solution), $O_2$(10-40%)-$CO_2$/$Mo^{6+}$-$M^{n+}$catalyst solution (M=Fe, Co, Ru, Cu, Zr, Hf, Ni, Zn).

* * * * *